(12) United States Patent
Zhao et al.

(10) Patent No.: US 11,744,472 B2
(45) Date of Patent: Sep. 5, 2023

(54) HEMODYNAMIC PARAMETER ESTIMATION BASED ON IMAGE DATA

(71) Applicant: GE PRECISION HEALTHCARE LLC, Wauwatosa, WI (US)

(72) Inventors: Zhoushe Zhao, Shanghai (CN); Yingbin Nie, Shanghai (CN); Chen Zhang, Shanghai (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 834 days.

(21) Appl. No.: 16/536,071

(22) Filed: Aug. 8, 2019

(65) Prior Publication Data

US 2021/0022617 A1    Jan. 28, 2021

(30) Foreign Application Priority Data

Jul. 22, 2019   (CN) .......................... 201910662652.4

(51) Int. Cl.
*G06T 3/00* (2006.01)
*A61B 5/021* (2006.01)
(Continued)

(52) U.S. Cl.
CPC .............. *A61B 5/021* (2013.01); *A61B 5/004* (2013.01); *G06T 5/30* (2013.01); *G06T 5/50* (2013.01); *G06T 7/0014* (2013.01); *G06T 7/11* (2017.01); *G06T 7/187* (2017.01); *G06T 2207/20081* (2013.01); *G06T 2207/20084* (2013.01); *G06T 2207/20216* (2013.01); *G06T 2207/30048* (2013.01); *G06T 2207/30104* (2013.01)

(58) Field of Classification Search
CPC ..... A61B 5/021; A61B 5/004; A61B 2576/02; A61B 6/5217; A61B 6/504; G06T 5/30; G06T 5/50; G06T 7/0014; G06T 7/11; G06T 7/187; G06T 2207/20081; G06T 2207/20084; G06T 2207/20216; G06T 2207/30048; G06T 2207/30104
See application file for complete search history.

(56) References Cited

U.S. PATENT DOCUMENTS 8,249,815 B2   8/2012   Taylor
8,315,812 B2   11/2012  Taylor
(Continued)

FOREIGN PATENT DOCUMENTS

EP   2633815 A1   9/2013

OTHER PUBLICATIONS

Shigeho Takarada, "An Angiographic Technique for Coronary Fractional Flow Reserve Measurement: Invivo Validation" Published online Aug. 31, 2012. (Year: 2012).*
(Continued)

*Primary Examiner* — Mekonen T Bekele
(74) *Attorney, Agent, or Firm* — Fletcher Yoder P.C.

(57) ABSTRACT

The present approach relates to determining a reference value based on image data that includes a non-occluded vascular region (such as the ascending aorta in a cardiovascular context). This reference value is compared on a pixel-by pixel basis with the CT values observed in the other vasculature regions. With this in mind, and in a cardiovascular context, the determined FFR value for each pixel is the ratio of CT value in the vascular region of interest to the reference CT value.

20 Claims, 6 Drawing Sheets

(51) Int. Cl.
  *G06T 7/187*  (2017.01)
  *G06T 7/11*   (2017.01)
  *A61B 5/00*   (2006.01)
  *G06T 5/30*   (2006.01)
  *G06T 5/50*   (2006.01)
  *G06T 7/00*   (2017.01)

(56) References Cited

U.S. PATENT DOCUMENTS

| | | |
|---|---|---|
| 8,496,594 B2 | 7/2013 | Taylor et al. |
| 8,523,779 B2 | 9/2013 | Taylor et al. |
| 8,812,245 B2 | 8/2014 | Taylor |
| 9,211,083 B2 | 12/2015 | Graziani et al. |
| 9,349,178 B1 | 5/2016 | Itu et al. |
| 9,700,219 B2 | 7/2017 | Sharma et al. |
| 9,974,453 B2 | 5/2018 | Fonte et al. |
| 10,010,255 B2 | 7/2018 | Fonte et al. |
| 10,034,614 B2 | 7/2018 | Edic et al. |
| 2007/0110294 A1* | 5/2007 | Schaap ............... G06V 10/30 382/131 |
| 2014/0005535 A1 | 2/2014 | Edie et al. |
| 2014/0086461 A1 | 3/2014 | Yao et al. |
| 2015/0087956 A1* | 3/2015 | Yao ................ A61B 6/022 600/407 |
| 2017/0258433 A1* | 9/2017 | Gulsun .............. A61B 6/5217 |
| 2017/0325769 A1 | 11/2017 | Venugopal et al. |
| 2017/0325770 A1 | 11/2017 | Edic et al. |
| 2018/0276817 A1 | 9/2018 | Isgum et al. |
| 2019/0172197 A1 | 6/2019 | Buckler et al. |
| 2019/0180880 A1 | 6/2019 | Lavi et al. |

OTHER PUBLICATIONS

Jerry T. Wong "Quantification of fractional flow reserve based on angiographic image data" Published online Jan. 7, 2011 (Year: 2011).*

PCT/EP2020/070688; International Search Report/Written Opinion dated Oct. 22, 2020; 12 pages.

U.S. Appl. No. 16/019,229, filed Jun. 26, 2018, Warner et al.

* cited by examiner

HEMODYNAMIC PARAMETER ESTIMATION BASED ON IMAGE DATA

CROSS-REFERENCE TO RELATED APPLICATION

This application claims priority to and the benefit of Chinese Patent Application No. 2019106626524, entitled "HEMODYNAMIC PARAMETER ESTIMATION BASED ON IMAGE DATA", filed Jul. 22, 2019, which is herein incorporated by reference in its entirety for all purposes.

TECHNICAL FIELD

The subject matter disclosed herein relates to estimation of cardiovascular parameters using suitable imaging modalities.

BACKGROUND

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

For example, Coronary Computed Tomography Angiography (CCTA) is an imaging application that has evolved with the introduction and improvement of computed tomography (CT), an imaging technology based on the observed transmission of X-rays through the patient for a range of angular positions that is sufficient for image reconstruction. With the introduction of multi-slice CT scanners (e.g., 4-slice, 16-slice, 64-slice and so forth) and faster rotation speeds (e.g., about 0.35 seconds to about 0.5 seconds for a full gantry rotation), it has become possible to generate useful images of the heart and associated cardiac vasculature. With current high-resolution (both spatial and temporal), 64-slice scanners, image quality is sufficient for CCTA to provide clinicians an imaging technique that has high sensitivity while still being able to generate images in a computationally efficient and timely manner.

Conversely, invasive coronary angiography (ICA) is also used in some contexts. However, ICA is an invasive and costly procedure (i.e., the procedure requires insertion of tools or devices, such as a pressure catheter, into the vascular vessels of the patient) and may still yield data of limited value. These factors limit the wide-spread use of ICA.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method is provided for estimating hemodynamic parameters. In accordance with this method, vasculature image data is acquired using an imaging system. The vasculature image data is segmented into a reference vessel region and into a vessel region of interest. A reference value is determined based on the reference vessel region. For each pixel of the vessel region of interest, determining a fractional flow reserve (FFR) pixel value based at least in part on a ratio of the original pixel value to the reference value. A FFR image is generated and displayed based at least in part on the FFR pixel values determined for the respective pixels of the vessel region of interest.

In a further embodiment, a processor-based system is provided. In accordance with this embodiment, the processor-based system comprises a processing component and a storage or memory encoding one or more processor-executable routines. The routines, when executed by the processing component, cause acts to be performed by the processor-based system comprising: accessing or acquiring vasculature image data; segmenting the vasculature image data into a reference vessel region and into a vessel region of interest; determining a reference value based on the reference vessel region; determining for each pixel of the vessel region of interest a fractional flow reserve (FFR) pixel value based at least in part on a ratio of the original pixel value to the reference value; and generating and displaying a FFR image based at least in part on the FFR pixel values determined for the respective pixels of the vessel region of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
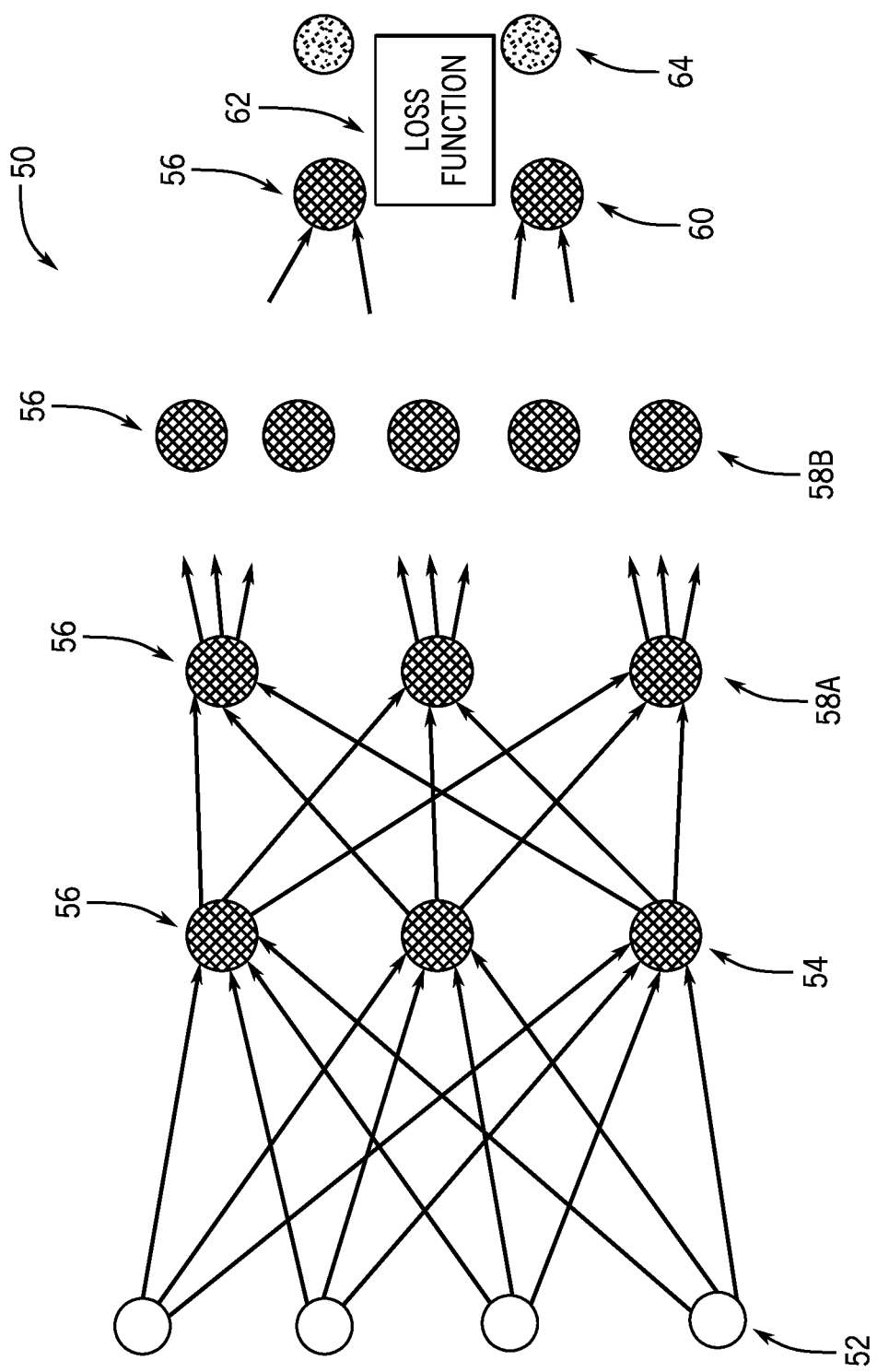
FIG. 1 depicts an example of an artificial neural network for training a deep learning model, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Further, though computed tomography (CT) examples are primarily provided herein, it should be understood that the disclosed technique may be used in other imaging modality contexts suitable for vascular imaging. For instance, the presently described approach may also be employed on data acquired by other types of tomographic scanners including, but not limited to, magnetic resonance imaging (Mill) scanners and/or other X-ray based imaging techniques, such as C-arm based techniques, tomosynthesis, fluoroscopy, and conventional radiographic (e.g., 2D) imaging.

By way of background, several imaging modalities, such as X-ray CT (e.g., multi-slice CT) and X-ray C-arm systems (e.g., cone-beam CT), measure projections of the object or patient being scanned where the projections, depending on the technique, correspond to Radon transform data, fan-beam transform data, cone-beam transform data, or non-uniform Fourier transforms. In other contexts, the scan data may be magnetic resonance data (e.g., Mill data) generated in response to magnetic fields and RF pulses, and so forth. Reconstruction routines and related correction and calibration routines are employed in conjunction with these imaging modalities to generate useful clinical images and/or data, which in turn may be used to derive or measure hemodynamic parameters of interest, as discussed herein.

With this in mind the present approach provides a non-invasive methodology for using images acquired using a suitable imaging modality to represent both anatomical and functional information for an imaged region. Such a non-invasive approach may provide reduced patient morbidity/mortality due to the elimination of unnecessary interventional procedures and may reduce healthcare costs for cardiac care. Though the discussion below focuses primarily on certain examples and contexts related to imaging a cardiac region (i.e., the heart and associated vasculature) it should be appreciated that such discussion is merely to facilitate explanation of the present techniques by providing a real-world context and examples. In practice, the present approach may be also suitable for use with respect to other vasculature and anatomic regions such as, but not limited to, the cranial region (i.e., cerebrovascular), the vascularization associated with the liver, the vascularization associated with the limbs (e.g., legs and arms), and so forth.

It may be further noted that the proposed approach provides benefits in terms of both speed of implementation and accuracy. For example, as discussed herein in one embodiment fractional flow reserve (FFR) values may be calculated or estimated in a pixel-by pixel manner, allowing an image to be generated in which each pixel has an associated estimate of FFR. Such an FFR image is based on actual measured image values (e.g., actual CT attenuation values in the context of CCTA) as opposed to modeled results or hypothetical extensions or extrapolations. As a result, this approach is more straight-forward in concept and computational-implementation and provided improved accuracy with respect to the anatomy of interest. Further, this process may be performed more quickly (e.g., 0.5 minute to 1 minute) than is typically possible in other conventional approaches, which may be of substantial benefit to the clinician and/or the patient as clinical results may be available at the time of a scan.

With this in mind, one embodiment of the present approach utilizes the anatomical information provided by Coronary Computed Tomography Angiography (CCTA). As noted above, though CT approaches such as CCTA are discussed herein, the present approaches may also be implemented using anatomical data measured and derived using other suitable imaging modalities, such as, but not limited to, magnetic resonance imaging (MM) or other radiographic X-ray imaging techniques. Explicit mention or discussion of CT imaging in the techniques described herein is merely intended to facilitate explanation by providing an example in a clinical context, and is not meant to be limiting with respect to the modalities that may be employed.

The present techniques utilize suitable vascular (e.g., cardiovascular) images (such as CCTA images in which the vasculature is contrast-enhanced using a suitable contrast agent) to estimate one or more hemodynamic parameters of interest, such as fractional flow reserve (FFR). As discussed in greater detail below, the present approach determines a reference value based on image data that includes a region of the ascending aorta (in the cardiovascular context). This reference value is compared on a pixel-by pixel basis with the CT values observed in the non-ascending aorta vasculature associated with the heart. With this in mind, and in this cardiovascular context, the determined FFR value for each pixel is the ratio of the coronary CT value of the respective pixel to the normal aortic CT value, which is a unitless number in the range from 0 to 1.

With the preceding introductory comments in mind, some generalized information is provided both to indicate general context of the present disclosure and to facilitate understanding and explanation of certain of the technical concepts described herein.

For example, as discussed herein, trained neural networks may be employed with respect to segmenting reconstructed or un-reconstructed image data (e.g., CCTA data). Neural networks as discussed herein may encompass deep neural networks, fully connected networks, convolutional neural networks (CNNs), perceptrons, auto encoders, recurrent networks, wavelet filter banks based neural networks, or other neural network architectures. These techniques may also be referred to herein as deep learning techniques, though this terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural networks for learning. By way of example, deep learning approaches may be characterized by their use of one or more processor-implemented routines to extract or model high level abstractions of a type of data of interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes, operations, or weightings of a given layer. In an image processing or reconstruction context, this may be characterized as different layers corresponding to the different feature levels or resolution in the data.

In general, the processing from one representation space to the next-level representation space can be considered as one 'stage' of the reconstruction process. Each stage of the reconstruction can be performed by separate neural networks or by different parts of one larger neural network. For example, as discussed herein, respective deep learning networks (e.g., trained neural network) may be used to perform vessel segmentation in acquired image data.

As discussed herein, as part of the initial training of deep learning processes to solve a particular problem, training data sets may be employed that have known initial values (e.g., input images, projection data, emission data, magnetic resonance data, and so forth) and known or desired values for a final output of the deep learning process. The training of a single stage may have known input values corresponding to one representation space and known output values corresponding to a next-level representation space. In this manner, the deep learning processes may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning processes, with the outputs then being compared to the outputs of the deep learning algorithm to validate the prior training and/or to prevent over-training.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Each layer, in this example, is composed of a plurality of "neurons" or nodes 56. The number of neurons 56 may be constant between layers or, as depicted, may vary from layer to layer. Neurons 56 at each layer generate respective outputs (such as based upon a weighting value associated with each neuron) that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed. The outputs of the final layer constitute the network output 60 which, in conjunction with a target image 64, may be used to compute some loss or error function 62 that can be backpropagated to guide the network training.

The loss or error function 62 measures the difference between the network output and the training target. In certain implementations, the loss function may be the mean squared error (MSE) of the voxel-level values or partial-line-integral values and/or may account for differences involving other image features, such as image gradients or other image statistics. Alternatively, the loss function 62 could be defined by other metrics associated with the particular task in question, such as a softmax function.

To facilitate explanation of the implementation of vessel segmentation in imaging system acquired data that may utilize certain deep learning techniques, the present disclosure primarily discusses these approaches in the context of a CT or C-arm system. However, it should be understood that the following discussion may also be applicable to other image modalities and systems including, but not limited to, MM and radiographic X-ray systems.

Figure 2:
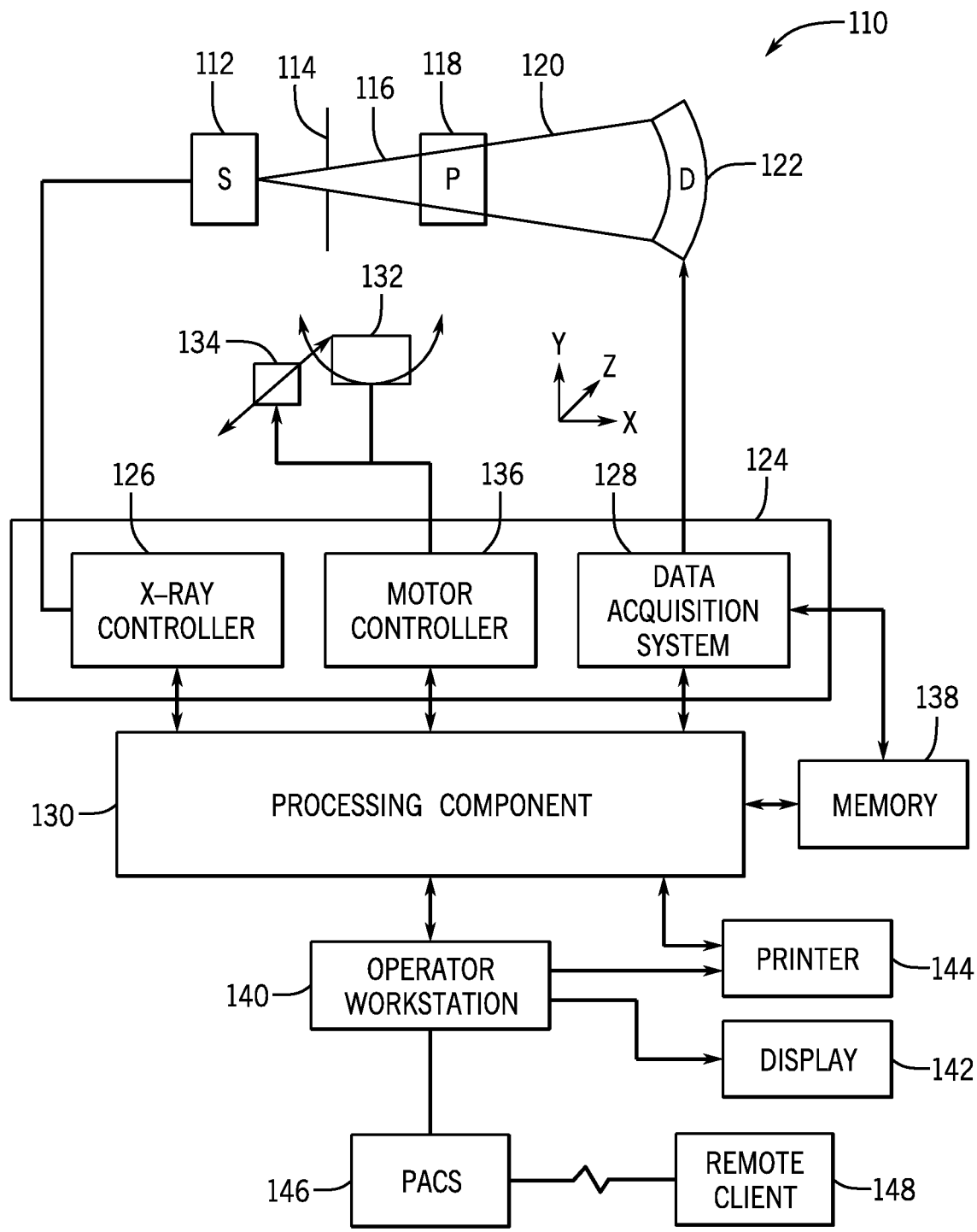
FIG. 2 is a block diagram depicting components of a computed tomography (CT) imaging system, in accordance with aspects of the present disclosure.

With this in mind, an example of an imaging system 110 (i.e., a scanner) is depicted in FIG. 2. In the depicted example, the imaging system 110 is a CT imaging system designed to acquire scan data (e.g., X-ray attenuation data) at a variety of views around a patient (or other subject or object of interest) and suitable for acquiring or generating cardiovascular parameters using the image data so acquired. In the embodiment illustrated in FIG. 2, imaging system 110 includes a source of X-ray radiation 112 positioned adjacent to a collimator 114. The X-ray source 112 may be an X-ray tube, a distributed X-ray source (such as a solid-state or thermionic X-ray source) or any other source of X-ray radiation suitable for the acquisition of medical or other images. In the case of MM, the measurements are samples in Fourier space and can either be applied directly as the input to the neural network or can first be converted to line integrals.

In the depicted example, the collimator 114 shapes or limits a beam of X-rays 116 that passes into a region in which a patient/object 118, is positioned. In the depicted example, the X-rays 116 are collimated to be a cone-shaped beam, i.e., a cone-beam, that passes through the imaged volume. A portion of the X-ray radiation 120 passes through or around the patient/object 118 (or other subject of interest) and impacts a detector array, represented generally at reference numeral 122. Detector elements of the array produce electrical signals that represent the intensity of the incident X-rays 120. These signals are acquired and processed to reconstruct images of the features within the patient/object 118.

Source 112 is controlled by a system controller 124, which furnishes both power, and control signals for CT examination sequences, including acquisition of two-dimensional localizer or scout images used to identify anatomy of interest within the patient/object for subsequent scan protocols. In the depicted embodiment, the system controller 124 controls the source 112 via an X-ray controller 126 which may be a component of the system controller 124. In such an embodiment, the X-ray controller 126 may be configured to provide power and timing signals to the X-ray source 112.

Moreover, the detector 122 is coupled to the system controller 124, which controls acquisition of the signals generated in the detector 122. In the depicted embodiment, the system controller 124 acquires the signals generated by the detector using a data acquisition system 128. The data acquisition system 128 receives data collected by readout electronics of the detector 122. The data acquisition system 128 may receive sampled analog signals from the detector 122 and convert the data to digital signals for subsequent processing by a processor 130 (e.g., a microprocessor, such as a CPU or GPU) as discussed below. Alternatively, in other embodiments the digital-to-analog conversion may be performed by circuitry provided on the detector 122 itself. The system controller 124 may also execute various signal processing and filtration functions with regard to the acquired image signals, such as for initial adjustment of dynamic ranges, interleaving of digital image data, and so forth.

In the embodiment illustrated in FIG. 2, system controller 124 is coupled to a rotational subsystem 132 and a linear positioning subsystem 134. The rotational subsystem 132 enables the X-ray source 112, collimator 114 and the detector 122 to be rotated one or multiple turns around the patient/object 118, such as rotated primarily in an x,y-plane about the patient. It should be noted that the rotational subsystem 132 might include a gantry or C-arm upon which the respective X-ray emission and detection components are disposed. Thus, in such an embodiment, the system controller 124 may be utilized to operate the gantry or C-arm.

The linear positioning subsystem 134 may enable the patient/object 118, or more specifically a table supporting the patient, to be displaced within the bore of the CT system 110, such as in the z-direction relative to rotation of the gantry. Thus, the table may be linearly moved (in a continuous or step-wise fashion) within the gantry to generate images of particular areas of the patient 118. In the depicted embodiment, the system controller 124 controls the movement of the rotational subsystem 132 and/or the linear positioning subsystem 134 via a motor controller 136.

In general, system controller 124 commands operation of the imaging system 110 (such as via the operation of the source 112, detector 122, and positioning systems described above) to execute examination protocols and to process acquired data. For example, the system controller 124, via the systems and controllers noted above, may rotate a gantry supporting the source 112 and detector 122 about a subject of interest so that X-ray attenuation data may be obtained at one or more views relative to the subject. In the present context, system controller 124 may also include signal processing circuitry, associated memory circuitry for storing programs and routines executed by the computer (such as routines for estimating or otherwise acquiring cardiovascular parameters of interest, as described herein), as well as configuration parameters, image data, and so forth.

In the depicted embodiment, the image signals acquired and processed by the system controller 124 are provided to a processing component 130 for processing in accordance with the presently disclosed techniques. Alternatively, processing of the signals or images reconstructed from the signals may be performed by one or more downstream processing components (such as may be present in a network connected workstation or server) for use in estimating cardiovascular function or properties. The processing component 130 may be one or more general or application-specific microprocessors. The data collected by the data acquisition system 128 may be transmitted to the processing component 130 directly or after storage in a memory 138. Any type of memory suitable for storing data might be utilized by such an exemplary system 110. For example, the memory 138 may include one or more optical, magnetic, and/or solid state memory storage structures. Moreover, the memory 138 may be located at the acquisition system site and/or may include remote storage devices for storing data, processing parameters, and/or routines for tomographic image reconstruction, as described below.

The processing component 130 may be configured to receive commands and scanning parameters from an operator via an operator workstation 140, typically equipped with a keyboard and/or other input devices. An operator may control the system 110 via the operator workstation 140. Thus, the operator may observe the reconstructed images and/or otherwise operate the system 110 using the operator workstation 140. For example, a display 142 coupled to the operator workstation 140 may be utilized to observe the reconstructed images and to control imaging. Additionally, the images may also be printed by a printer 144 which may be coupled to the operator workstation 140.

Further, the processing component 130 and operator workstation 140 may be coupled to other output devices, which may include standard or special purpose computer monitors and associated processing circuitry. One or more operator workstations 140 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 140 may also be coupled to a picture archiving and communications system (PACS) 146. PACS 146 may in turn be coupled to a remote client 148, radiology department information system (RIS), hospital information system (HIS) or to an internal or external network, so that others at different locations may gain access to the raw or processed image data or estimates of cardiovascular parameters derived from such image data.

While the preceding discussion has treated the various exemplary components of the imaging system 110 separately, these various components may be provided within a common platform or in interconnected platforms. For example, the processing component 130, memory 138, and operator workstation 140 may be provided collectively as a general or special purpose computer or workstation configured to operate in accordance with the aspects of the present disclosure. In such embodiments, the general or special purpose computer may be provided as a separate component with respect to the data acquisition components of the system 110 or may be provided in a common platform with such components. Likewise, the system controller 124 may be provided as part of such a computer or workstation or as part of a separate system dedicated to image acquisition or processing of image data.

The system of FIG. 2 may be utilized to acquire projection data for a variety of views about a region of interest of a patient to reconstruct images of the imaged region using the scan data. Projection (or other) data acquired by a system such as the imaging system 110 may be processed as discussed herein to generate or estimate one or more hemodynamic parameters of interest.

With the preceding background and context discussion in mind, the present disclosure relates to an accurate and stable technique for calculating CT coronary fractional flow reserve. As used herein, fractional flow reserve (FFR) is the ratio of the blood flow obtained by a coronary artery in which stenosis (e.g., a stenotic lesion) is present relative to the maximum blood flow obtained without stenosis.

Certain implementations of the technique discussed herein employ aspects of deep learning and the principle of radioactive tracer technology to generate and process images (e.g., contrast-enhanced CCTA images, Mill images, and so forth) to calculate FFR values with respect to the images. As may be appreciated, drug intervention enlarges the blood vessels to maximum and a CCTA (or comparable) scan is performed at this peak. This is equivalent to calculating coronary blood flow with deconvolution of special points. This is the theoretical basis of radioactive tracer method as discussed and relied upon herein.

Figure 3:
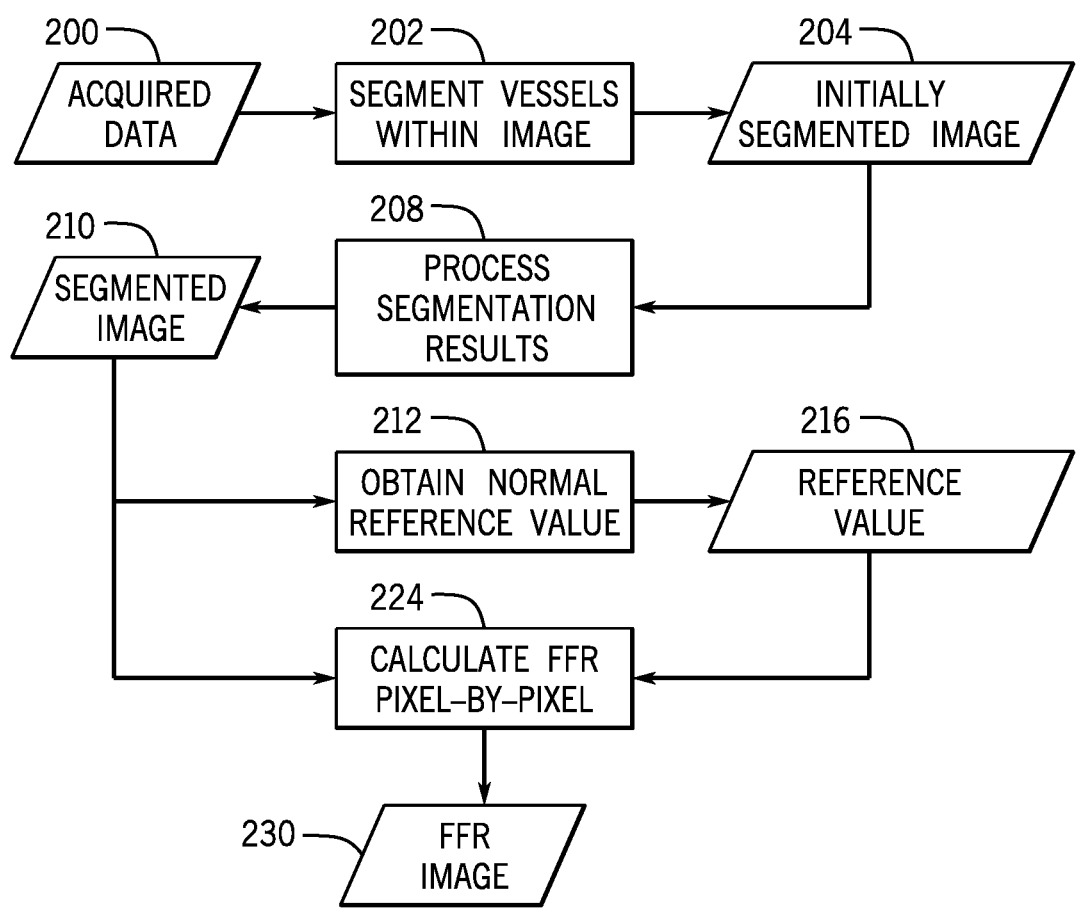
FIG. 3 depicts a process flow of steps for determining a fractional flow reserve based on image data, in accordance with aspects of the present disclosure.

Turning to FIG. 3, an overview of steps employed in accordance with one implementation of the present approach are provided in the form of a process flow. In this example a vessel segmentation step 202 is performed on data 200 acquired by an imaging system (e.g., a three-dimensional (3D) CCTA image, I(x,y,z)) of the vasculature (e.g., a cardiac image) of a patient, so as to segment the coronary artery and aorta within the image. Though the present examples use the terminology of an image or segmented image for convenience and to provide context to the data inputs and outputs, it should be understood that the some or all aspects of the segmentation step described herein may be performed on unreconstructed data, i.e., without initial reconstruction to the image domain, depending on the training of the respective neural network. Conversely, the present approach may also be performed on reconstructed images in the image domain if the respective neural network is so trained.

Figure 4:
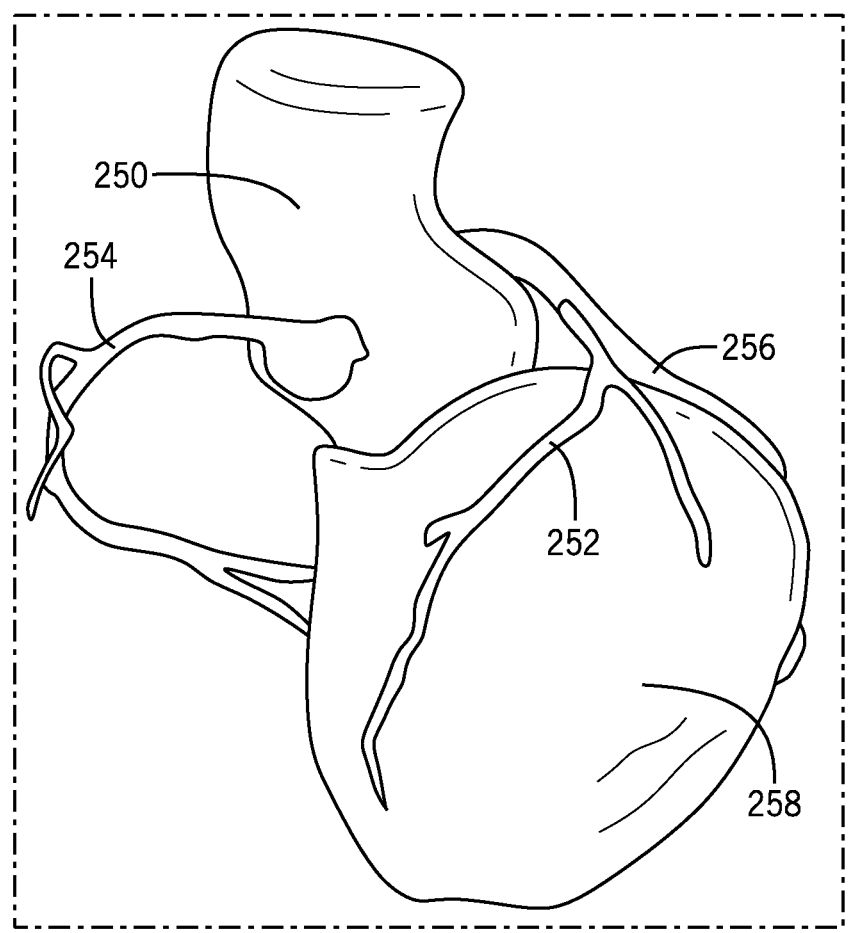
FIG. 4 depicts a segmented cardiac image, in accordance with aspects of the present disclosure.

With this in mind, in one embodiment, the vessel segmentation of step 202 is performed using a deep learning network (such as a trained dense V-network or VNet) trained to process CCTA images (or other suitable images of vascular structure) provided as an input. In such an example, the trained neural network generates as an output one or more initially segmented images 204. The initially segmented image 204 may be, in one implementation, a binary segmentation into an aortic region ($A_{Aorta}$) (in which pixels are labeled in a binary fashion as being or not being part of the aortic region), shown by reference number 250 in FIG. 4, and a coronary artery region ($A_{Coronary}$) (in which pixels are labeled in a binary fashion as being or not being part of the coronary artery region). In this example, the binary image of the coronary artery region ($A_{Coronary}$) may be further automatically divided into the left anterior descending artery (shown by reference number 252), the right coronary artery (shown by reference number 254), and the left circumflex artery (shown by reference number 256) which together compose the coronary artery region $A_{Coronary}$. In the depiction of FIG. 4, the left ventricle 258 is also shown for anatomic context.

In certain embodiments the segmentation results (e.g., initially segmented image 204) may be further processed (e.g., optimized) (step 208) to generate the segmented image 210. For example, in certain implementations processing the initial segmentation results may involve automatically setting seed points within $A_{Coronary}$ and $A_{Aorta}$ based on defined selection rules. A region growing technique may then be employed with respect to the seed points to fill out and/or better define one or more of the segmented regions, resulting in the segments $A_{PostCoronary}$ and $A_{PostAorta}$ in the present context. Such an approach may be useful for eliminating or re-characterizing pixels or small pixel regions within a given image region that were not properly labeled by the initial deep learning based segmentation. By way of example, such a region growing approach may be useful to remove irrelevant noise points and to otherwise clean up or improve the segmentation results $A_{PostCoronary}$ and $A_{PostAorta}$. In this manner, each image 200 (e.g., CCTA images) may be properly segmented with respect to the image segments of interest.

In a next step, with respect to the ascending aorta area segment of a given segmented image 210, a normal reference value 216 of the ascending aorta region is obtained (step 212). The ascending aorta area segment is selected as the reference, in this example, because the clinical risk of aortic occlusion is zero, thus providing accuracy and stability to the measurement result. In one such example, the region $A_{PostAorta}$ is eroded by a morphological operation (i.e., morphological erosion) to shrink the binary image inward. This operation helps reduce the impact and/or effect of the vessel wall on those factors that might be influenced by the vessel wall. Next a convolution is performed on the original image corresponding to the region $A_{PostAorta}$ (i.e., not the morphologically eroded image). For example, a mean convolution may be performed on $A_{PostAorta}$ using a 3×3×3 mask so as to obtain a set of one-dimensional vectors. Noise points of the one-dimensional vectors can then be removed using a distance-based noise detection technique. The normal reference value (r) 216 of the ascending aorta region is then obtained by averaging the one-dimensional vectors from which the noise has been removed.

Subsequently, in the depicted example, a fractional flow reserve (FFR) image 230 is calculated (step 224) on a pixel-by-pixel basis such that each pixel of the image 230 has an associated FFR value. In one example this process may be performed by performing a pixel-by-pixel comparison of the pixel values of the segmented coronary region(s) (e.g., determined from segmented image 210) with the determined normal region reference value 216. In one implementation the determined FFR values at the respective pixels are, for each pixel, the ratio of coronary contrast media uptake to the aortic reference point. With this in mind, FFR as determined as discussed herein, can directly represent the vessel FFR. Due to the calculation being performed on a pixel-by-pixel basis, changes at each anatomical point (as reflected in the image data) are taken into account and FFR may be calculated directly in or for a given vascular area.

By way of further example, in one implementation of a pixel-by-pixel FFR calculation, assuming the original image pixel value corresponding to the binary image $A_{PostCoronary}$ is p(x,y,z), the FFR calculation may be in accordance with:

$$I_{FFR}(x, y, z) = \begin{cases} \dfrac{p(x, y, z) - \text{Min}_{Coronary}}{r - \text{Min}_{Coronary}}, & \text{if } p(x, y, z) \leq r \\ 1, & \text{if } p(x, y, z) > r \end{cases} \quad (1)$$

where r is the normal reference value of the ascending aorta region.

Figure 5:
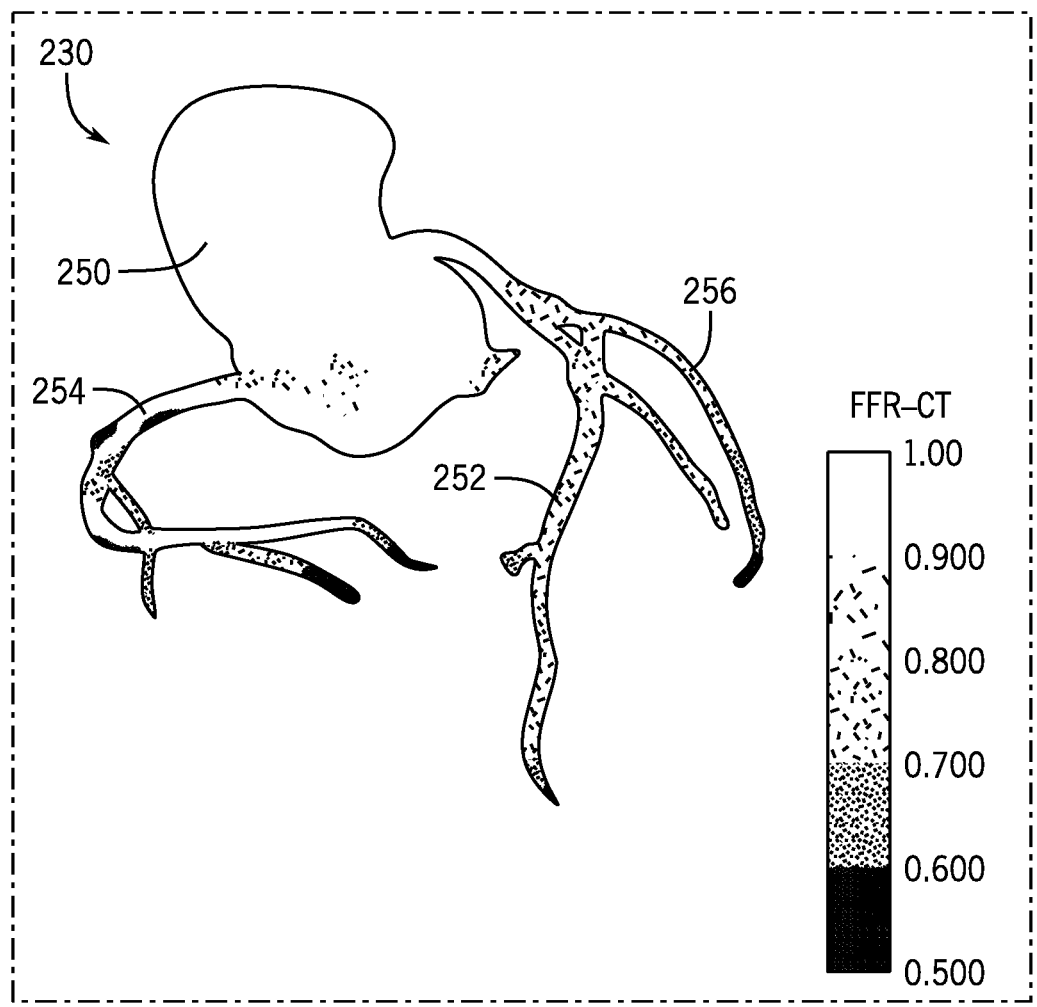
FIG. 5 depicts an image that conveys fractional flow reserve information in a pixel-by-pixel manner, in accordance with aspects of the present disclosure.

In this example, the FFR values of the region $A_{PostAorta}$ (i.e., the aorta area) are set to 1 to reflect the absence of occlusion on the ascending aorta. Three-dimensional traversal is then performed for $I_{FFR}(x,y,z)$. If the pixel value of (x, y, z) is less than a specified threshold value (e.g., 0.55 in one example), the FFR value of point (x, y, z) is replaced by the mean value of the point (x, y, z) five-pixel neighborhood (or some similar measure of central tendency for the region centered on the pixel location in question). If the pixel value of point (x, y, z) is greater than or equal to the threshold value (e.g., 0.55 in the current example), it remains unchanged. In this manner, the final FFR value is obtained for each point (x, y, z), i.e., there is an associated FFR value for each pixel so that the FFR is calculated in a pixel-by-pixel manner, resulting in an FFR image 230. An example of a FFR image 230 is shown in FIG. 5, in which the anatomic regions shown in FIG. 4 are labeled so as to facilitate explanation. As may be seen the aortic region 250 for which the reference value r was derived is substantially homogeneous in terms of the measured FFR. Conversely, in the downstream vasculature where there is the possibility of stenotic lesions and/or other obstructions it can be seen that the FFR values may be less than what is seen in the aortic region, indicating possible circulatory problems. As may be appreciated, the FFR image 230 can be used to measure (e.g., quantify) the extent or degree of vascular stenosis in a given vessel or vessel region based on the area-based or diameter-based approaches for measuring occlusion. Further, as shown in this example, the present FFR approach can calculates FFR in multiple (here three) blood vessels concurrently and considers blood flow redistribution, which has clinical value.

It may be noted that the proposed approach for calculating FFR, as illustrated in the FFR image 230, is based on actual measured image values (e.g., actual CT attenuation values in the context of CCTA) as opposed to modeled results or hypothetical extensions or extrapolations. As a result, this approach is more straight-forward in concept and implementation. Further, this process may be performed more quickly (e.g., 0.5 minute to 1 minute) than is typically possible in other conventional approaches, which may be of substantial benefit to the clinician and/or the patient as clinical results may be available at the time of a scan, allowing follow-up actions to be performed in a timely manner. Further the present approach provides data with higher accuracy than conventional approaches, as estimations of the values of interest occur in a pixel-by-pixel manner, as opposed to being more broadly modeled.

Figure 6:
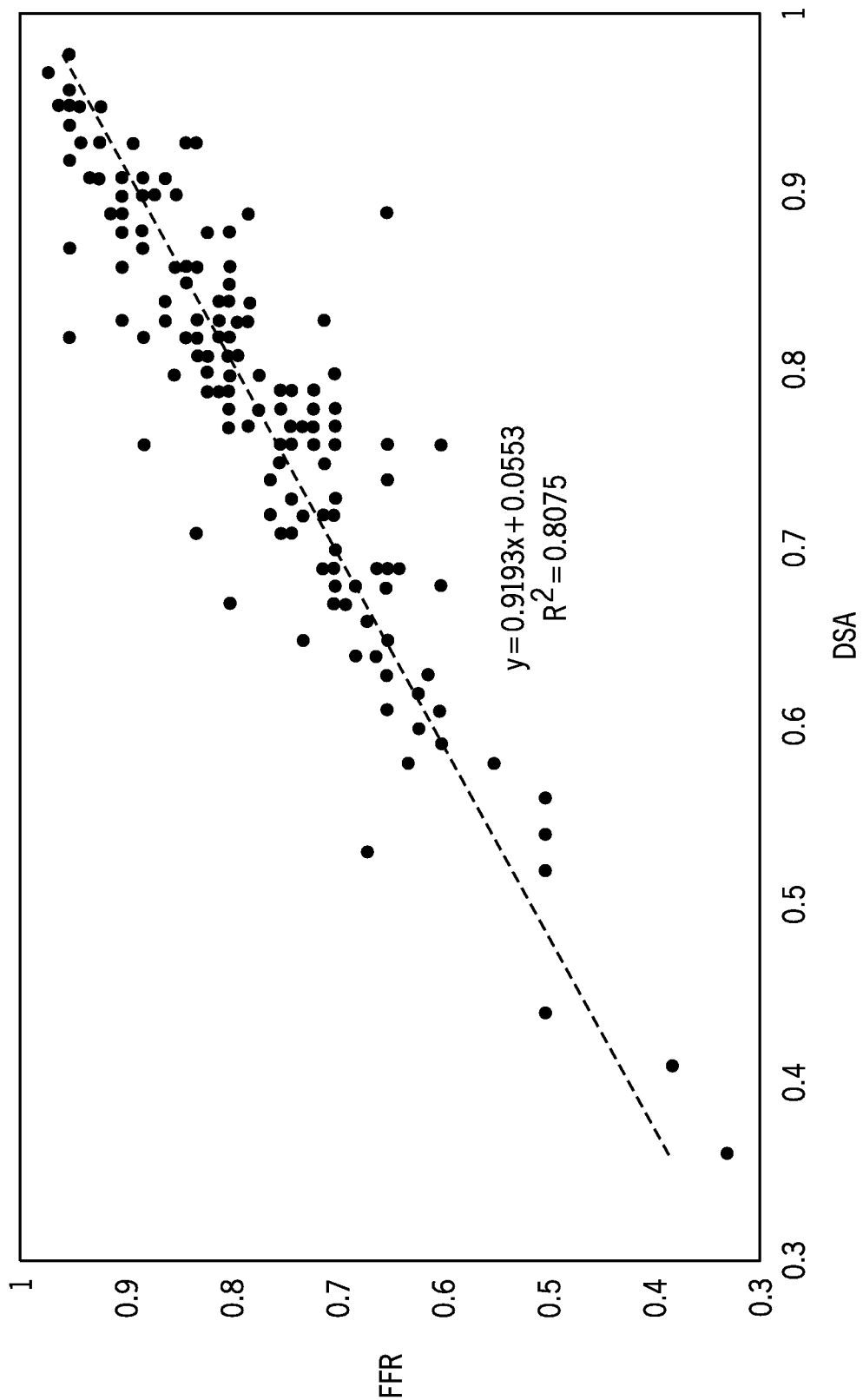
FIG. 6 depicts a plot conveying correlation between FFR values derived in accordance with image-based techniques (vertical-axis) compared with the clinically-determined (DSA) FFR values (horizontal axis), in accordance with aspects of the present disclosure.

To demonstrate the efficacy of the present approach, a study was performed in which 163 coronary vascular vessels from 135 patients were used to test the accuracy of the present image-based FFR calculation technique. The FFR values derived in accordance with the techniques described herein (vertical axis) were compared with the clinical FFR values (determined from digital subtraction angiography (DSA)) (horizontal axis) with linear regression analysis. A plot of the results is shown in FIG. 6. The decision coefficient $R^2$ was 0.808, which showed high correlation between FFR values determined using the present techniques and the clinical measured FFR and indicated high accuracy of the present techniques in calculating FFR values.

Technical effects of the invention include, but are not limited to, determining a reference value based on image data that includes a non-occluded vascular region (such as the ascending aorta in a cardiovascular context). This reference value is compared on a pixel-by pixel basis with the CT values observed in the other vasculature regions. With this in mind, and in a cardiovascular context, the determined FFR value for each pixel is the ratio of CT value in the respective vascular region to the reference CT value.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating hemodynamic parameters, comprising the steps of:
    acquiring vasculature image data using an imaging system, wherein the vasculature image data is acquired utilizing coronary computed tomography angiography;
    segmenting the vasculature image data into a reference vessel region and into a vessel region of interest;
    determining a reference value based on the reference vessel region;
    determining for each pixel of the vessel region of interest a fractional flow reserve (FFR) pixel value based at least in part on a ratio of the original pixel value to the reference value; and
    generating and displaying a FFR image based at least in part on the FFR pixel values determined for the respective pixels of the vessel region of interest, wherein the FFR image is of both the reference vessel region and the vessel region of interest, and a respective FFR pixel value is conveyed in a pixel by pixel manner for each pixel of the reference vessel region and the vessel region of interest within the FFR image.

2. The method of claim 1, wherein the vasculature image data comprises cardiac image data.

3. The method of claim 1, wherein the imaging system comprises a computed tomography (CT) imaging system.

4. The method of claim 1, wherein segmenting the vasculature image data comprises:
    providing the vascular image data as an input to a neural network trained to perform a binary segmentation of the vasculature image data with respect to the reference vessel region and the vessel region of interest.

5. The method of claim 1, wherein the reference vessel region comprises an aortic region and the vessel region of interest comprises a coronary artery region.

6. The method of claim 5, wherein the coronary artery region is further segmented into a left anterior descending artery, a right coronary artery, and a left circumflex artery.

7. The method of claim 1, further comprising the step of:
    processing the reference vessel region and the vessel region of interest by:
        selecting one or more seed points;
        performing a region growing technique using the one or more seed points to eliminate or re-characterize mis-labeled pixels within the reference vessel region and the vessel region of interest.

8. The method of claim 1, wherein the reference value is determined for the reference vessel region by:
    performing a morphological erosion on the reference vessel region;
    performing a convolution on the reference vessel region to obtain a set of one-dimensional vectors;
    averaging the one-dimensional vectors to generate the reference value.

9. The method of claim 1, wherein the FFR pixel value for each pixel of the vessel region of interest is a ratio of coronary contrast media uptake to the reference value at each respective pixel.

10. The method of claim 1, further comprising the step of:
    based on the FFR image, measuring an extent of vascular stenosis in a vessel or vessel region based on one of area or diameter.

11. A processor-based system, comprising:
    a processing component; and
    a storage or memory encoding one or more processor-executable routines, wherein the routines, when executed by the processing component, cause acts to be performed by the processor-based system comprising:
        accessing or acquiring vasculature image data, wherein the vasculature image data is acquired utilizing coronary computed tomography angiography;
        segmenting the vasculature image data into a reference vessel region and into a vessel region of interest;
        determining a reference value based on the reference vessel region;
        determining for each pixel of the vessel region of interest a fractional flow reserve (FFR) pixel value based at least in part on a ratio of the original pixel value to the reference value; and generating and displaying a FFR image based at least in part on the FFR pixel values determined for the respective pixels of the vessel region of interest, wherein the FFR image is of both the reference vessel region and the vessel region of interest, and a respective FFR pixel value is conveyed in a pixel by pixel manner for each pixel of the reference vessel region and the vessel region of interest within the FFR image.

12. The processor-based system of claim 11, wherein the vasculature image data comprises cardiac image data.

13. The processor-based system of claim 11, wherein the processor-based system comprises a computed tomography (CT) imaging system.

14. The processor-based system of claim 11, wherein segmenting the vasculature image data comprises:

providing the vascular image data as an input to a neural network trained to perform a binary segmentation of the vasculature image data with respect to the reference vessel region and the vessel region of interest.

15. The processor-based system of claim 11, wherein reference vessel region comprises an aortic region and the vessel region of interest comprises a coronary artery region.

16. The processor-based system of claim 15, wherein the coronary artery region is further segmented into a left anterior descending artery, a right coronary artery, and a left circumflex artery.

17. The processor-based system of claim 11, wherein the routines, when executed by the processing component, cause further acts to be performed by the processor-based system comprising:

processing the reference vessel region and the vessel region of interest by:
selecting one or more seed points;
performing a region growing technique using the one or more seed points to eliminate or re-characterize mis-labeled pixels within the reference vessel region and the vessel region of interest.

18. The processor-based system of claim 11, wherein the reference value is determined for the reference vessel region by:

performing a morphological erosion on the reference vessel region;
performing a convolution on the reference vessel region to obtain a set of one-dimensional vectors;
averaging the one-dimensional vectors to generate the reference value.

19. The processor-based system of claim 11, wherein the FFR pixel value for each pixel of the vessel region of interest is a ratio of coronary contrast media uptake to the reference value at each respective pixel.

20. The processor-based system of claim 11, wherein the routines, when executed by the processing component, cause further acts to be performed by the processor-based system comprising:

based on the FFR image, measuring an extent of vascular stenosis in a vessel or vessel region based on one of area or diameter.

* * * * *